United States Patent
McKee et al.

(10) Patent No.: US 10,846,852 B2
(45) Date of Patent: Nov. 24, 2020

(54) REDUCTION OF BACKGROUND SIGNAL IN BLOT IMAGES

(71) Applicant: Bio-Rad Laboratories, Inc., Hercules, CA (US)

(72) Inventors: Clayton T. McKee, Davis, CA (US); Michael Griffin, El Cerrito, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 227 days.

(21) Appl. No.: 15/850,405

(22) Filed: Dec. 21, 2017

(65) Prior Publication Data

US 2018/0182100 A1  Jun. 28, 2018

Related U.S. Application Data

(60) Provisional application No. 62/438,664, filed on Dec. 23, 2016.

(51) Int. Cl.
*G06T 7/00* (2017.01)
*G06T 7/155* (2017.01)
(Continued)

(52) U.S. Cl.
CPC ......... *G06T 7/0014* (2013.01); *G01N 27/447* (2013.01); *G01N 33/54393* (2013.01);
(Continued)

(58) Field of Classification Search
CPC .. G06T 2207/10056; G06T 5/30; G06T 7/155
See application file for complete search history.

(56) References Cited

U.S. PATENT DOCUMENTS 4,742,552 A * 5/1988 Andrews .................. G06T 1/20
                                                382/303
4,783,751 A * 11/1988 Ehrlich .................. G01N 15/088
                                                345/581

(Continued)

OTHER PUBLICATIONS

John C. Russ & J. Christian Russ, "Introduction to Image Processing and Analysis", Taylor & Francis, CRC Press. (Year: 2017).*

(Continued)

*Primary Examiner* — Gandhi Thirugnanam
(74) *Attorney, Agent, or Firm* — Kilpatrick Townsend and Stockton LLP

(57) ABSTRACT

Systems and methods for producing blot images. A blot, for example a western blot, is imaged using an imaging system having a field of view and a magnification. Features of interest in the blot correspond to features in the digital image, and the sizes of the features in the digital image depend on the magnification of the imaging system. A structuring element is selected based on the sizes and shapes of the features in the digital image, and the image is morphologically eroded and dilated varying numbers of times. The eroded and dilated image is subtracted from the original blot image to remove background signal from the blot image, producing an output image. The number of erosions needed to completely erode the features of interest is determined automatically, for example by investigating the behavior of the kurtosis of the output image as a function of the number of erosions performed.

17 Claims, 16 Drawing Sheets

(51) Int. Cl.
| | | |
|---|---|---|
| *G06T 7/194* | (2017.01) | |
| *G06T 5/50* | (2006.01) | |
| *G01N 33/58* | (2006.01) | |
| *G01N 33/543* | (2006.01) | |
| *G01N 27/447* | (2006.01) | |
| *G06T 5/00* | (2006.01) | |
| *G06T 5/30* | (2006.01) | |
| *G01N 21/76* | (2006.01) | |
| *G01N 21/64* | (2006.01) | |
| *G01N 21/59* | (2006.01) | |

(52) U.S. Cl.
CPC ............ *G01N 33/582* (2013.01); *G06T 5/001* (2013.01); *G06T 5/30* (2013.01); *G06T 5/50* (2013.01); *G06T 7/155* (2017.01); *G06T 7/194* (2017.01); *G01N 21/5911* (2013.01); *G01N 21/6456* (2013.01); *G01N 21/76* (2013.01); *G01N 27/44721* (2013.01); *G06T 2207/10056* (2013.01); *G06T 2207/10064* (2013.01); *G06T 2207/20036* (2013.01); *G06T 2207/20224* (2013.01); *G06T 2207/30024* (2013.01)

(56) References Cited

U.S. PATENT DOCUMENTS

| | | | | |
|---|---|---|---|---|
| 5,048,109 A * | 9/1991 | Bloomberg | G06K 9/20 382/164 |
| 5,257,182 A * | 10/1993 | Luck | G01N 15/1468 382/224 |
| 5,436,984 A * | 7/1995 | Sarkkinen | G06T 5/30 382/258 |
| 5,848,189 A * | 12/1998 | Pearson | B41F 33/0036 382/218 |
| 5,960,127 A * | 9/1999 | Davis | G06T 5/30 358/447 |
| 6,141,460 A * | 10/2000 | Amer | H04N 1/4092 382/199 |
| 6,155,978 A * | 12/2000 | Cline | G01S 7/52026 128/916 |
| 6,192,160 B1 * | 2/2001 | Sunwoo | G06K 9/44 382/257 |
| 6,236,769 B1 * | 5/2001 | Desai | G06T 5/30 382/277 |
| 6,259,807 B1 * | 7/2001 | Ravkin | G01N 15/1475 382/133 |
| 6,282,328 B1 * | 8/2001 | Desai | G06T 5/30 382/205 |
| RE37,668 E | 4/2002 | Etoh | |
| 6,404,934 B1 * | 6/2002 | Lee | G06T 5/30 382/260 |
| 6,633,662 B2 | 10/2003 | Ravkin | |
| 6,771,834 B1 * | 8/2004 | Martins | G06T 7/11 382/173 |
| 7,142,732 B2 * | 11/2006 | Bamford | G06T 7/11 382/308 |
| 7,162,095 B2 * | 1/2007 | Chen | H04N 19/176 375/E7.029 |
| 7,515,764 B2 * | 4/2009 | Mitsutani | G06T 5/30 382/257 |
| 7,602,531 B2 * | 10/2009 | Bailey | G06K 15/02 358/3.15 |
| 8,160,382 B2 * | 4/2012 | Sefcik | G06K 9/3233 382/103 |
| 8,571,343 B2 * | 10/2013 | Chen | G06K 9/36 382/260 |
| 8,606,012 B2 * | 12/2013 | Suzuki | G06K 9/00067 382/100 |
| 2001/0028510 A1 * | 10/2001 | Ramm | G06T 7/75 359/663 |
| 2001/0049114 A1 * | 12/2001 | Bacus | G01N 33/57484 435/7.21 |
| 2002/0183601 A1 * | 12/2002 | Tearney | A61B 1/00082 600/310 |
| 2004/0101912 A1 * | 5/2004 | Rubin | B82Y 5/00 435/7.2 |
| 2004/0114829 A1 * | 6/2004 | LeFeuvre | G06T 5/005 382/275 |
| 2005/0053268 A1 * | 3/2005 | Breen | G01N 27/44721 382/128 |
| 2005/0063568 A1 * | 3/2005 | Sun | G06K 9/00234 382/117 |
| 2005/0238248 A1 * | 10/2005 | Mitsutani | G06T 5/30 382/257 |
| 2006/0067591 A1 * | 3/2006 | Guzzwell | G06K 9/00228 382/289 |
| 2006/0088202 A1 * | 4/2006 | Venkatachalam | G06T 5/30 382/152 |
| 2006/0159328 A1 * | 7/2006 | Vaz | G06K 9/44 382/131 |
| 2007/0217668 A1 * | 9/2007 | Bornemann | G06K 9/00 382/132 |
| 2008/0002873 A1 * | 1/2008 | Reeves | G06T 11/008 382/133 |
| 2009/0041322 A1 * | 2/2009 | Wolf | G06K 9/44 382/131 |
| 2018/0182100 A1 * | 6/2018 | McKee | G06T 7/0014 |

OTHER PUBLICATIONS

International Search Report and Written Opinion from Application No. PCT/US2017/067858, dated Mar. 9, 2018.
Singh, P et al.; "Non Uniform Background Removal using Morphology based Structuring Element for Particle Analysis"; *International Journal of Computer Applications* (0975-8887); vol. 33, No. 6; Nov. 2011; pp. 11-16.
Extended European Search Report in EP Application 17884261.3 dated Jul. 27, 2020; 8 pages.
Kimori, Y.; "Morphological image processing for quantitative shape analysis of biomedical structures: effective contrast enhancement"; *Journal of Synchrotron Radiation*; vol. 20, No. 6; Nov. 1, 2013; pp. 848-853.
Hiary, H. et al.; "A system for segmenting and extracting paper-based watermark designs"; *International Journal on Digital Libraries*; Heidelberg, Germany; vol. 6, No. 4; Jul. 1, 2007; pp. 351-361.
Clouard, R.; "Tutorial: Mathematical Morphology"; Oct. 9, 2016; downloaded at https://web.archive.org/web/20161009090916/https://clouard.users.greyc.fr/Pantheon/experiments/morphology/index-en.html.
Gassmann, M. et al.; "Quantifying Western blots: Pitfalls of densitometry"; *Electrophoresis*; vol. 30, No. 11; Jun. 1, 2009; pp. 1845-1855.

* cited by examiner

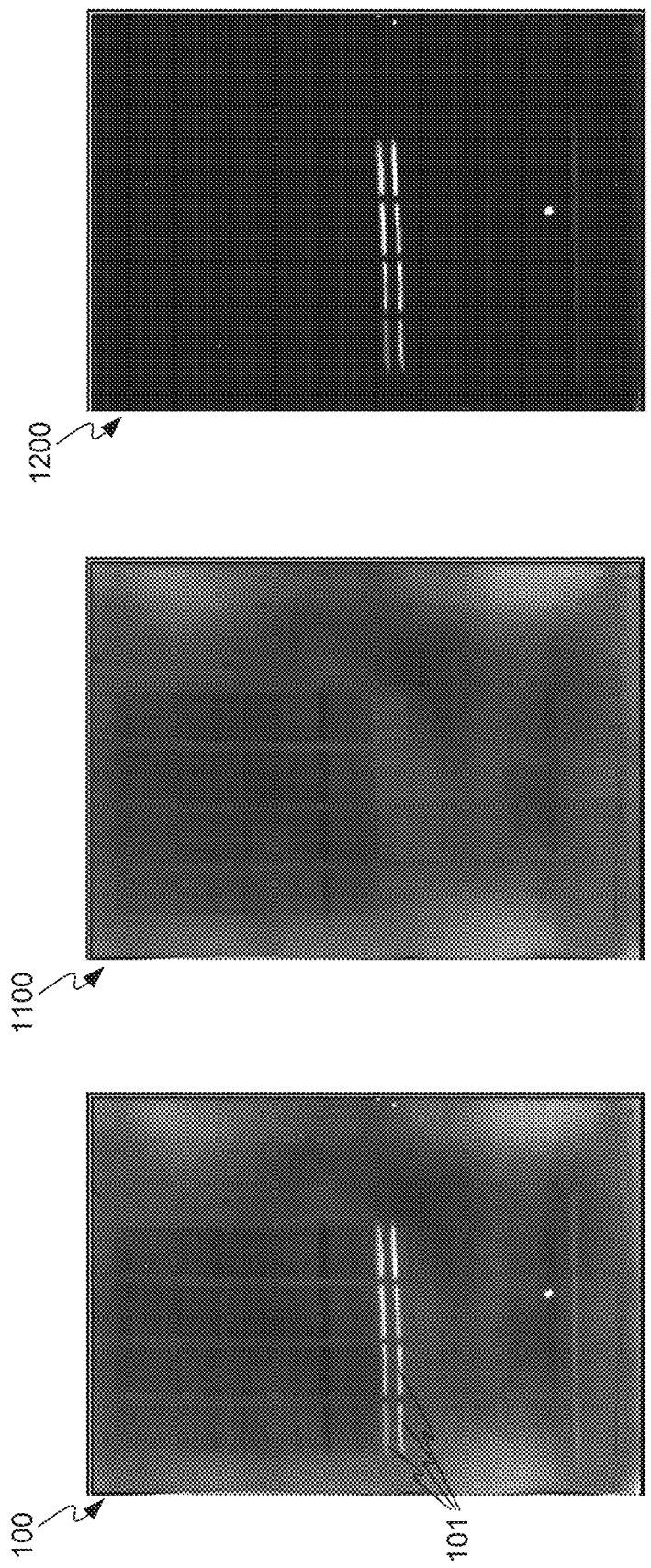

REDUCTION OF BACKGROUND SIGNAL IN BLOT IMAGES

This application claims the benefit of U.S. Application 62/438,664 filed on Dec. 23, 2016, which is hereby incorporated by reference in its entirety for all purposes.

BACKGROUND OF THE INVENTION

The principle of electrophoresis is widely used in biochemical research and analysis, for example to separate and quantify proteins in a mixture, for disease diagnosis, for DNA analysis, or for other purposes. The mixture is supplied to the edge of a gel and placed within an electric field. The electric field causes the proteins in the mixture move through the gel. The rate at which each protein moves depends on the molecular weight of the particular protein, such that lighter proteins move through the gel faster than heavier proteins. After a time, the different proteins become separated into bands within the gel.

In some cases, the gel may be stained and washed, so that the locations of the proteins can be read directly. However, in another common technique known as a western blot, the proteins are transferred to a nitrocellulose membrane and exposed to a primary antibody that recognizes the protein of interest. A labeled secondary antibody that binds to the primary antibody is then introduced. For example, the secondary antibody may be labeled with a fluorescent or chemiluminescent marker. Once excess antibody is removed, the pattern of protein on the nitrocellulose membrane can be read, for example by exciting fluorescence of the marker antibodies and reading the pattern of the resulting fluorescent light emanated from the sample, or by reading the pattern of light emanated from the sample by chemiluminescence. The pattern may be read, for example, using a camera or scanner sensitive to the wavelength of the emanated light, and may be recorded in a digital image. The protein bands show up as features within the digital image.

Images of western blots often contain significant background signals that may surround the features of interest. This background signal may result from non-uniform binding of the marked antibody, fluorescence of the substrate, or from other sources. The background signal is undesirable, as it obscures the features of interest in the digital image and makes further analysis more difficult.

Other kinds of techniques, for example dot blotting, Southern blotting, and others, produce images of blots having similar background signal issues.

BRIEF SUMMARY OF THE INVENTION

According to one aspect, a system comprises an imaging device having a field of view and a magnification. The imaging device is configured to produce a first digital image of a biological blot having features of interest. The digital image includes the features of interest, and the sizes of the features of interest in the first digital image are determined in part by the magnification of the imaging device. The shapes of the features of interest in the first digital image are determined in part by a particular technique used to produce the blot. The system further comprises a processor programmed to select a structuring element, the size and shape of the structuring element being selected at least in part based on the sizes and shapes of the features of interest in the first digital image. The processor is further configured to perform morphological erosion of the first digital image using the structuring element to produce a second digital image. The morphological erosion is performed a number of times needed to completely erode the features of interest from the first digital image. The processor is further configured to subsequently perform morphological dilation of the second digital image using the structuring element to produce an eroded and dilated image. The morphological dilation is performed the same number of times as the morphological erosion. The processor is further configured to produce an output digital image by subtracting the eroded and dilated digital image from the first digital image. The number of times needed to completely erode the features of interest is determined automatically. In some embodiments, the imaging device may be a camera, a scanner, or a densitometer. In some embodiments, the blot emanates light by fluorescence, and the imaging device produces the first digital image by measuring the light emanated from the blot by fluorescence. In some embodiments, the blot emanates light by chemiluminescence, and the imaging device produces the first digital image by measuring the light emanated from the blot by chemiluminescence. In some embodiments, the blot is an electrophoretic sample, and the sizes and shapes of the features of interest are determined in part by the particular electrophoretic technique used to prepare the blot.

According to another aspect, a method of removing background from a digital image of a biological blot comprises receiving a first digital image of a biological blot having features of interest. The first digital image is produced by an imaging device having a field of view and a magnification, and the digital image includes the features of interest. The sizes of the features of interest in the first digital image are determined in part by the magnification of the imaging device, and the shapes of the features of interest in the first digital image are determined in part by a particular technique used to produce the blot. The method further comprises selecting a structuring element. The size and shape of the structuring element is selected at least in part based on the sizes and shapes of the features of interest in the first digital image. The method further includes performing morphological erosion of the first digital image using the structuring element to produce a second digital image, the morphological erosion being performed a number of times needed to completely erode the features of interest. The method further includes subsequently performing morphological dilation of the second digital image using the structuring element to produce an eroded and dilated image, the morphological dilation being performed the same number of times as the morphological erosion. The method further includes producing an output digital image by subtracting the eroded and dilated digital image from the first digital image. The number of times needed to completely erode the features of interest is determined automatically. In some embodiments, an equal number of erosions and dilations constitute a set of erosions and dilations, the erosions and dilations are performed in sets having increasing numbers of erosions and dilations, and the method further comprises automatically determining after each set of erosions and dilations whether the features of interest have been completely eroded. In some embodiments, automatically determining whether the features of interest have been completely eroded further comprises: producing a respective output image after each set of erosions and dilations; calculating a kurtosis of the respective output image after each set of erosions and dilations; tracking the rate of change of the kurtosis as a function of the number of erosions and dilations in each set of erosions and dilations; comparing the rate of change of the kurtosis with a predetermined threshold; and determining that the features of interest have been completely eroded when the rate of change of the kurtosis falls below the predetermined threshold. In some embodiments, an equal number of erosions and dilations constitute a set of erosions and dilations, and the method further comprises: performing the erosions and dilations in sets having varying numbers of erosions and dilations; calculating a kurtosis of the respective output image after each set of erosions and dilations; and modeling the rate of change of the kurtosis as an exponential decay of the rate as a function of the number of erosions and dilations in each set of erosions and dilations. In some embodiments, the method further comprises fitting a straight line to the logarithms of at least some of the measured rates of change of kurtosis as a function of the number of erosions and dilations performed in each set of erosions and dilations, and calculating where the straight line has a zero ordinate. In some embodiments, the method further comprises selecting as a desired output image the output image corresponding to the number of erosions and dilations at which the straight line has a zero ordinate. In some embodiments, receiving a first digital image of a biological blot comprises receiving a digital image of an electrophoretic sample. In some embodiments, the sizes and shapes of the features of interest in the first digital image are determined at least in part by the particular electrophoretic technique used to prepare the blot. In some embodiments, receiving a first digital image of a biological blot comprises receiving a digital image of a western blot. In some embodiments, receiving a first digital image of a biological blot comprises receiving a digital image of a dot blot.

According to another aspect, a method of removing background from a digital image of a biological blot comprises receiving a first digital image of a biological blot having features of interest, and selecting a structuring element. The size and shape of the structuring element are selected at least in part based on the sizes and shapes of the features of interest in the first digital image. The method further comprises performing morphological erosion of the first digital image using the structuring element to produce a second digital image. The morphological erosion is performed a number of times needed to completely erode the features of interest. The method further includes subsequently performing morphological dilation of the second digital image using the structuring element to produce an eroded and dilated image. The morphological dilation is performed the same number of times as the morphological erosion. The method further includes producing an output digital image by subtracting the eroded and dilated digital image from the first digital image. The number of times needed to completely erode the features of interest is determined automatically. In some embodiments, automatically determining whether the features of interest have been completely eroded further comprises: producing a respective output image after each set of erosions and dilations; calculating a kurtosis of the respective output image after each set of erosions and dilations; and determining whether the features of interest have been completely eroded from a particular one of the output images based on the behavior of the kurtosis as a function of the number of erosions and dilations in each set of erosions and dilations. In some embodiments, determining whether the features of interest have been completely eroded from a particular one of the output images based on the behavior of the kurtosis as a function of the number of erosions and dilations in each set of erosions and dilations comprises: calculating a rate of change of the kurtosis as a function of the number of erosions and dilations in each set of erosions and dilations; and determining whether the features of interest have been completely eroded from a particular one of the output images based on the behavior of the rate of change of the kurtosis as a function of the number of erosions and dilations in each set of erosions and dilations.

BRIEF DESCRIPTION OF THE DRAWINGS

FIG. 10 shows the original blot image of FIG. 1 again, for convenient reference.

FIG. 11 shows an eroded and dilated image, in accordance with embodiments of the invention.

FIG. 12 shows an output image in accordance with embodiments of the invention, being the difference between the images of FIGS. 10 and 11.

DETAILED DESCRIPTION OF THE INVENTION

Figure 1:
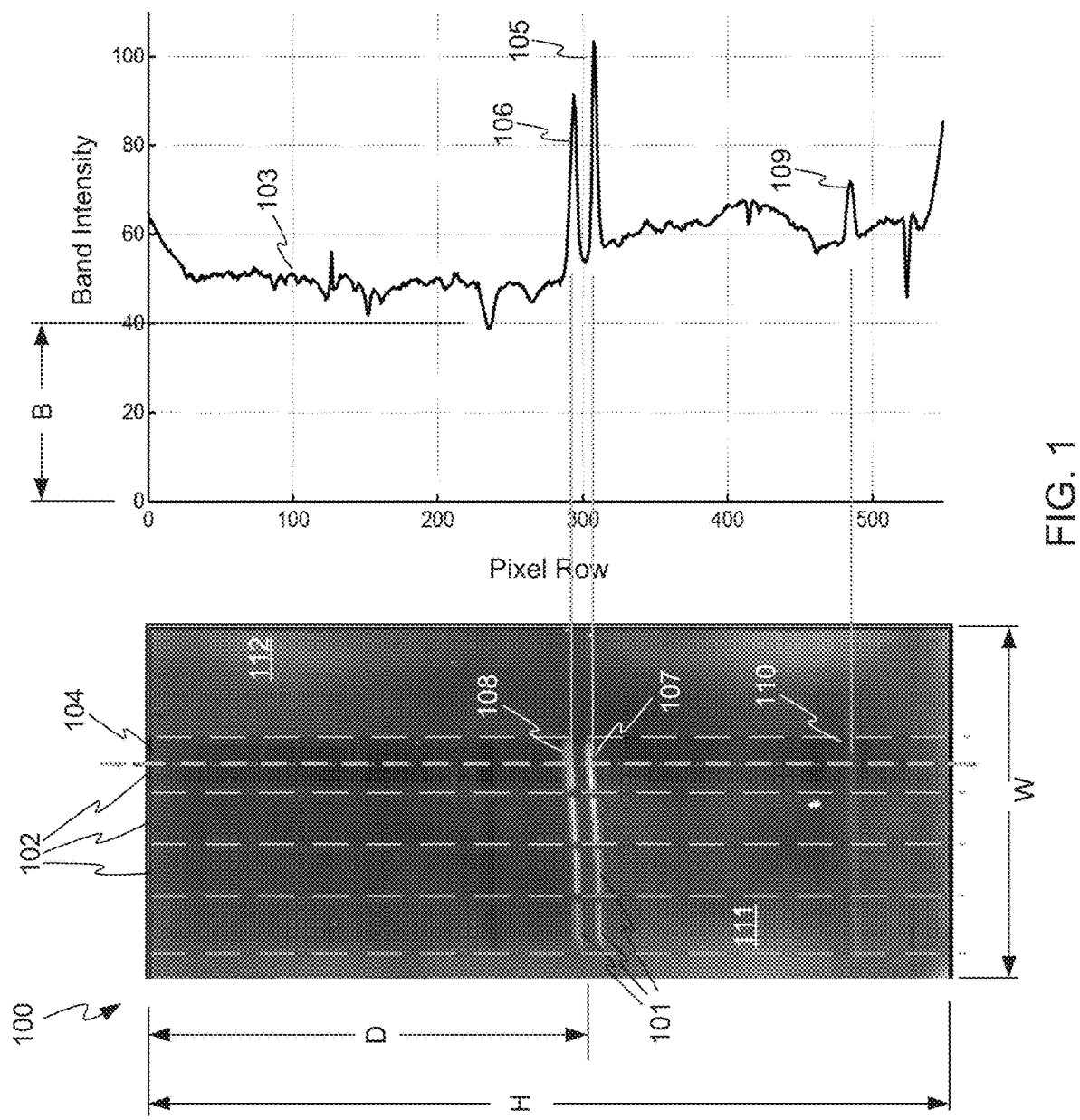
FIG. 1 illustrates an example image of a western blot, usable in embodiments of the invention.

FIG. 1 illustrates an example image 100 of a western blot, usable in embodiments of the invention. In this example, the blot included tagged proteins of interest emanating light by fluorescence, and these proteins result in bright features or bands 101 in the image (only a few of which are labeled). The features are roughly rectangular, as a result of the particular technique used to prepare the blot. As is inferable from image 100, the blot was made using four lanes 102 of a gel, the approximate boundaries of which are superimposed on image 100 in FIG. 1. The proteins responsible for the features of interest 101 traveled a distance corresponding roughly to "D" in each lane during the electrophoresis step of creating the western blot.

Image 100 has a width W and a height H, measured in pixels and determined by the size of the imaged blot, the magnification of the imaging device used to make the image, and the number of pixels in sensor used to make the image. For example, for a western blot made using a gel 70×85 millimeters imaged by a camera that projects the blot onto an image sensor having 2750×2200 pixels, each of lanes 102 will be about 170 pixels wide. Accordingly, features 101 in FIG. 1 are roughly 170×30 pixels and are roughly rectangular. In other embodiments, the sizes and shapes of the features of interest as represented in an image may be different, depending on the characteristics of the device used to make the image and the technique used to make the blot.

It will be recognized that image 100 is a relatively simple example, in which the same mixture has been placed in each of lanes 102, so that the lanes show similar results. In other examples, multiple bands may be visible in any of the lanes, and the lanes may be supplied with different mixtures.

In image 100, each pixel is represented by a value between 0 and 255, indicating the amount of light collected by the imaging system at each respective pixel location. Values in the range of 0-255 can be conveniently represented using 8-bit digital values. In other embodiments, different bit depths may be used. For example, each pixel in the image may be represented by a 16-bit value, so that 65,536 different brightness levels are possible. Also in image 100, brighter pixels correspond to locations on the blot emanating more light. In other embodiments, the opposite may be true, depending on the sign convention adopted by the imaging system and associated processing.

Also shown in FIG. 1 is an intensity trace 103 of one particular column 104 of image 100. The intensity trace 103 shows the pixel values of each of the pixels along a line down column 104. Peaks 105 and 106 correspond to bright features 107 and 108 in image 100. A smaller peak 109 corresponds to a dimmer feature 110 in image 100.

It is apparent in FIG. 1 that intensity trace 103 is displaced by at least distance B from the axis of the trace. That is, none of the pixels in image 100 has an intensity value of zero, which would represent a completely black pixel. This is because of background signal in the image. The background signal is non-uniform, and shows as varying levels of low-level brightness. Some areas more prominent background signal are shown at 111 and 112.

This background signal is for the most part not an artifact of the imaging system used to generate digital image 100 from the blot. Even when the imaging system has been calibrated to account for such effects as illumination non-uniformity, lens vignetting, and the like, the background signal remains because it is an actual signal from the substrate of the blot.

Embodiments of the invention provide apparatus and methods for automatically removing the background signal from a digital blot image.

Figure 2:
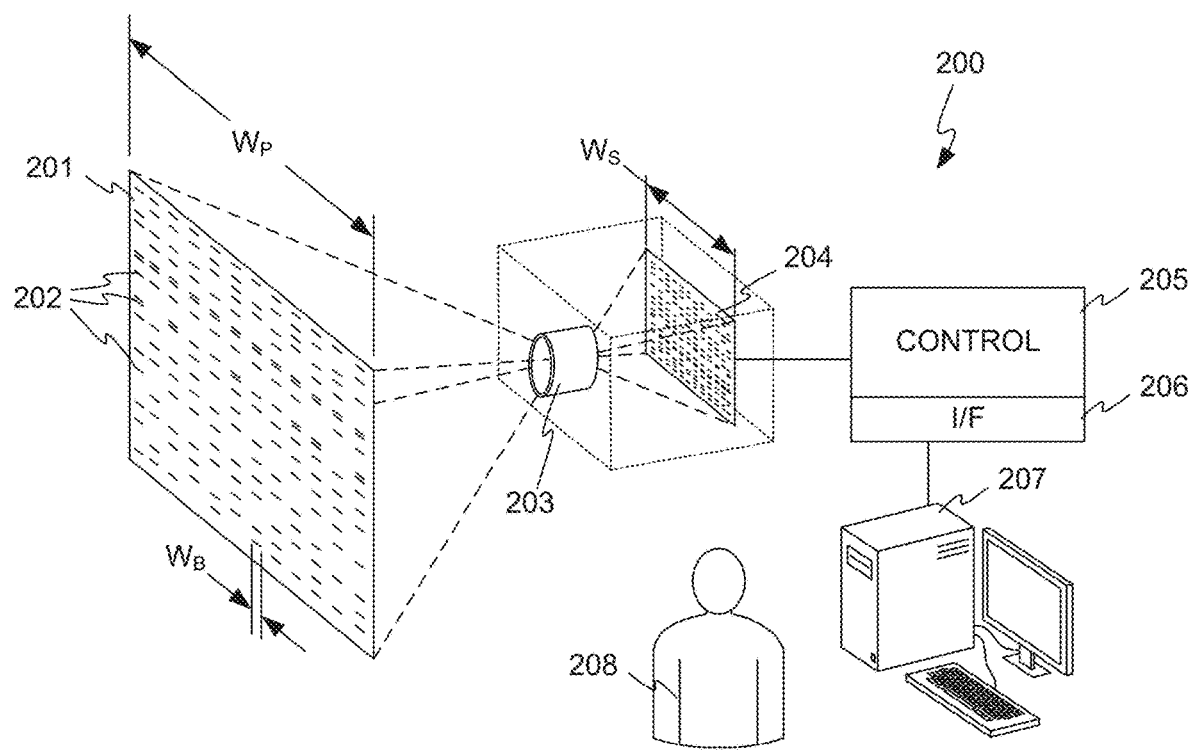
FIG. 2 illustrates an imaging system in accordance with embodiments of the invention, suitable for creating images of blots such as the image shown in FIG. 1.

FIG. 2 illustrates an imaging system 200 in accordance with embodiments of the invention, suitable for creating images of blots such as image 100 shown in FIG. 1. Imaging system 200 may be thought of as a camera. Some structural details are omitted from FIG. 2 for clarity.

In FIG. 2, blotting paper 201 has been developed such that bands 202 appear. For example, bands 202 may fluoresce when illuminated by an illumination light source (not shown). The wavelength of the fluorescent light depends on the particular fluorophore used to label the blot developed on blotting paper 201, and may be in the infrared, visible, or ultraviolet portion of the spectrum.

Light from blotting paper 201 is collected and focused by lens 203 onto a sensor 204. Sensor 204 may be, for example, a charge coupled device (CCD) sensor, a complementary metal oxide semiconductor (CMOS) sensor, or another kind of sensor. Typically, the sensor includes light-sensitive areas called "pixels" that accumulate electrical charge at a rate proportional to the intensity of the light falling on them. The pixels may be reset and the sensor exposed to light for a fixed time. After a time, each pixel will have accumulated charge in an amount corresponding to the brightness of the light being produced by its corresponding location on blotting paper 201. The charges are converted to voltage signals representing the light intensity sensed at the sensor pixels, and the voltage signals are further converted to digital values. An ordered array of these digital values may be called a digital image. The individual values in the digital image (or sets of values representing color components of light reaching the sensor pixels) may also be called "pixels". The meaning of "pixel" is generally clear from the context. The conversion from charge levels to numerical values may be performed by control electronics 205, shown in FIG. 2. Control electronics 205 are shown as a single block, but may contain various digital and analog electronic components, one or more analog-to-digital (A/D) converters, or other components, in any suitable arrangement. Control electronics 205 may provide the digital image via interface 206 to a computer system 207, for viewing by a user 208 and further processing. Other architectures are possible within the scope of the appended claims. For example, an A/D converter may be integrated with sensor 204, so that control electronics 205 receive already-digitized values.

The magnification of system 200 is the ratio of the width $W_S$ of the image projected by lens 203 onto sensor 204 to the width $W_P$ of the area imaged of blotting paper 201. Thus, the width in millimeters of one of bands 202 on sensor 204 is $$M_M = W_B \text{ (mm)} * W_S \text{ (mm)} / W_P \text{ (mm)}$$

and the width in pixels of one of bands 202 is given $$P = M_M / W_S * W$$

where W is the width in pixels of the resulting digital image. The height of a particular band in pixels at the sensor will depend somewhat on the particular assay being performed, but will often be smaller than the width of the band in pixels at the sensor, in the case of a western blot image.

Figure 3:
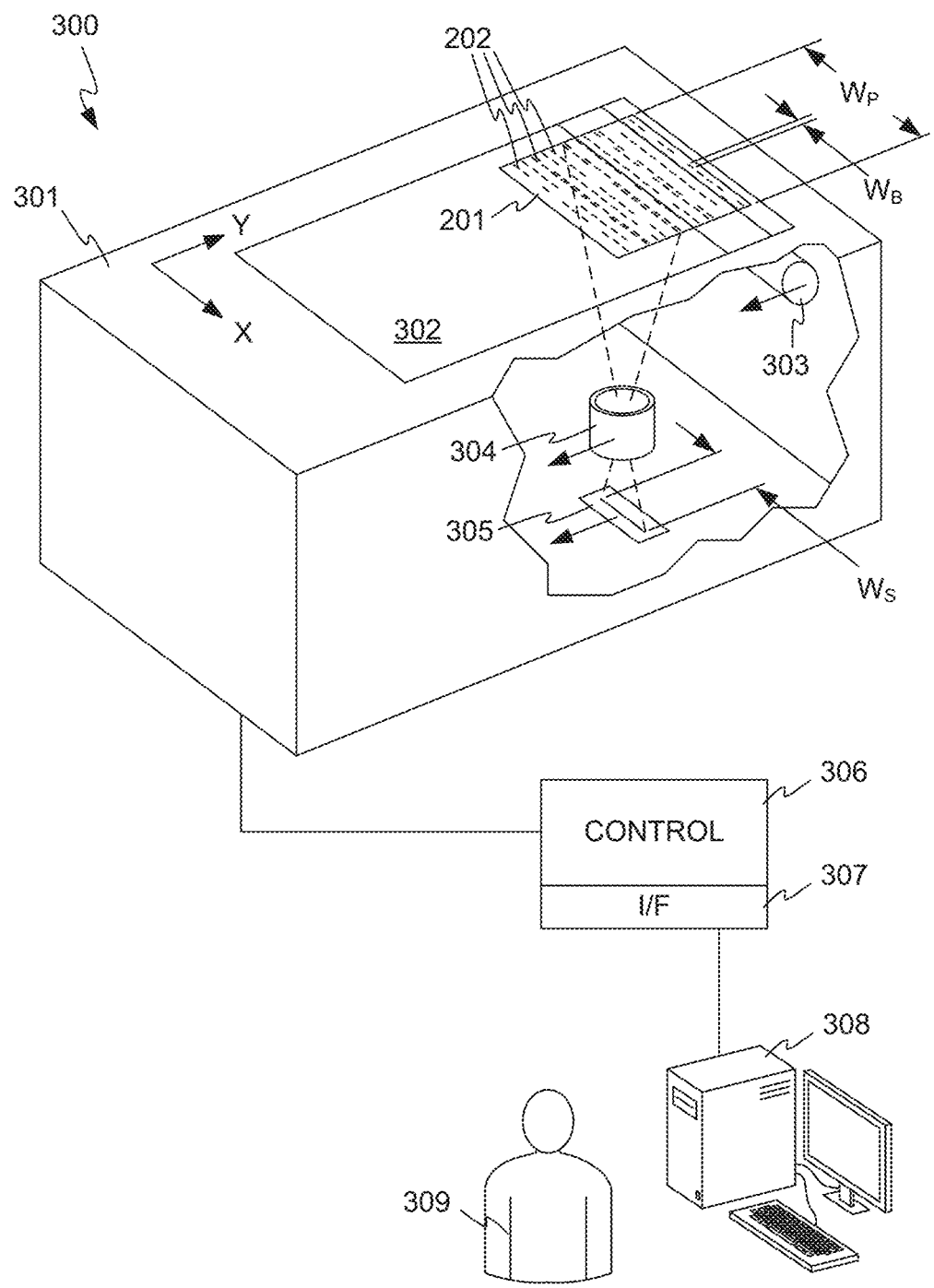
FIG. 3 illustrates another imaging system in accordance with embodiments of the invention, suitable for creating images of blots such as the image shown in FIG. 1.

FIG. 3 illustrates another imaging system 300 in accordance with embodiments of the invention, suitable for creating images of blots such as image 100 shown in FIG. 1. Imaging system 300 includes a scanner 301, sometimes also called a densitometer. Scanner 301 includes a cover glass 302, on which blotting paper 201 is placed. In this example, a light source 303, lens 304, and linear image sensor 305 are swept under cover glass 302 to read blotting paper 201. The details of the motion system and structure joining light source 303, lens 304, and sensor 305 together are omitted for clarity.

Light source 303 may be any suitable kind of light source, for example a light emitting diode (LED) light source that produces light for exciting fluorescence from blotting paper 201. Lens 304 gathers some of the emitted fluorescent light and focuses it on sensor 305. Various baffles, filters, or other features (not shown) may be in place to block reflected illumination light from reaching sensor 305.

Sensor 305 may be a CCD sensor, a CMOS sensor, or another suitable kind of sensor. The conversion from charge levels in sensor 305 to numerical values may be performed by control electronics 306, shown in FIG. 3. Control electronics 306 are shown as a single block, but may contain various digital and analog electronic components, one or more analog-to-digital (A/D) converters, or other components, in any suitable arrangement. Control electronics 306 may provide the digital image via interface 307 to a computer system 308, for viewing by a user 309 and further processing.

Sensor 305 differs from sensor 204 discussed above in that sensor 305 may have only a single row or a small number of rows of pixel sites. Thus the field of view of sensor 305, as projected onto blotting paper 201, encompasses only a narrow strip of blotting paper 201, crossing blotting paper 201 in the X direction shown in FIG. 3. This field of view is scanned across blotting paper 201 in the Y direction by a motion system (not shown), and an image of blotting paper 201 is accumulated by successive exposures of sensor 305 to successive strips of blotting paper 201. A two-dimensional image of blotting paper 201 is constructed from the strip images. Other architectures are possible within the scope of the appended claims. For example, an A/D converter may be integrated with sensor 305, so that control electronics 306 receive already-digitized values.

The magnification of system 300 is the ratio of the width $W_S$ of the image projected by lens 304 onto sensor 305 to the width $W_P$ of the area imaged of blotting paper 201. Thus, the width in millimeters of one of bands 202 on sensor 305 is $$M_M = W_B \text{ (mm)} * W_S \text{ (mm)} / W_P \text{ (mm)}$$

and the width in pixels of one of bands 202 is given $$P = M_M / W_S * W$$

where W is the width in pixels of the resulting digital image. As with imaging system 200, the height of a particular band in pixels will depend somewhat on the particular assay being performed, but will often be smaller than the width of the band in pixels at the sensor, in the case of a western blot image.

Other kinds of imaging systems are possible within the scope of the appended claims, for producing an image such as digital image 100.

Prior methods of removing background signal from an image such as image 100 have encountered drawbacks. For example, global image adjustments such as increasing contrast may effectively force some or all of the background areas of the image to zero, but do not account for background signal that is variable across the image. The prior "rolling disk" technique may be sensitive to the size of the disk chosen, and therefore may not be repeatable between users of the system.

In embodiments of the invention, morphological image processing operations are used to remove the background signal in an automated manner. Although known, the morphological operations of erosion and dilation are described below for completeness.

Morphological operations process an image based on the shapes of features in the image, and not merely based on pixel brightness levels. In morphological operations, pixel values are adjusted based on the values of neighboring pixels. The pixels considered to be in the neighborhood of a particular pixel are defined by a structuring element, also sometimes called a kernel. The size and shape of the structuring element can make the morphological operation sensitive to the sizes and shapes of features in the image.

The size and shape of the kernel are preferably selected based on the sizes and shapes of the features of interest in the blot image. For example, for processing an image of a western blot, the kernel may be rectangular and have a height of 0.1, 0.2, 0.3, 0.5, or another proportion of the heights of features of interest expected in the image. Thus, if features 20 pixels high are expected, the kernel may be 3-11 pixels high. (While not an absolute requirement, the kernel should have an odd number of rows and an odd number of columns.) Other ratios are possible.

For processing an image of a dot blot, the kernel may be two-dimensional and the non-zero values in the kernel may approximate a filled circle, so as to operate uniformly on the entire edge of a generally-circular dot feature. As before, the diameter of the circle may be selected as a proportion of the expected diameters of dots in the image.

Figures 4, 5A, 5B, 5C:
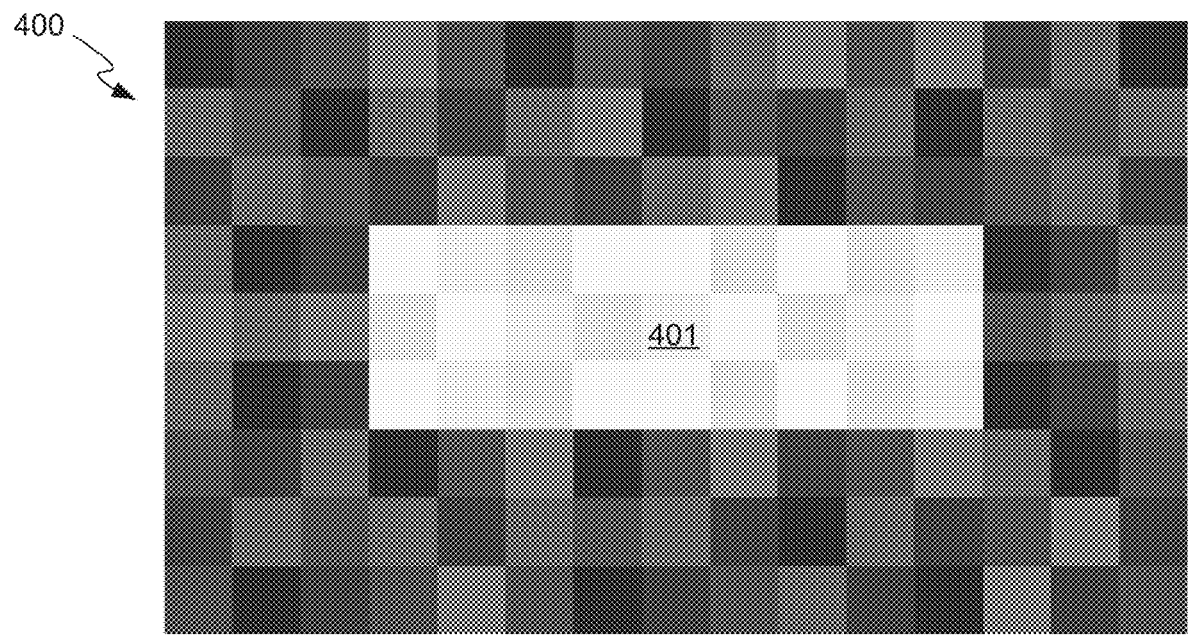
FIG. 4 illustrates a small idealized digital image, enlarged so that individual pixels are distinguishable, and suitable for describing the morphological operation of erosion.
FIGS. 5A-5C illustrate example structuring elements or kernels.

FIG. 4 illustrates a small idealized first digital image 400, enlarged so that individual pixels are distinguishable, and suitable for describing the morphological operation of erosion. Image 400 is 15 pixels wide by 9 pixels high, and has a prominent central high-intensity feature 401, whose pixels are much brighter (in this example) than the background pixels surrounding it. Feature 401 is 9 pixels wide by 3 pixels high.

FIGS. 5A-5C illustrate an example structuring elements or kernels 500. Kernels 501 and 502 may be especially suited for processing images having rectangular features, for example images of western blots. Kernel 503 may be especially suited for processing images having round features, for example images of dot blots.

Figure 6:
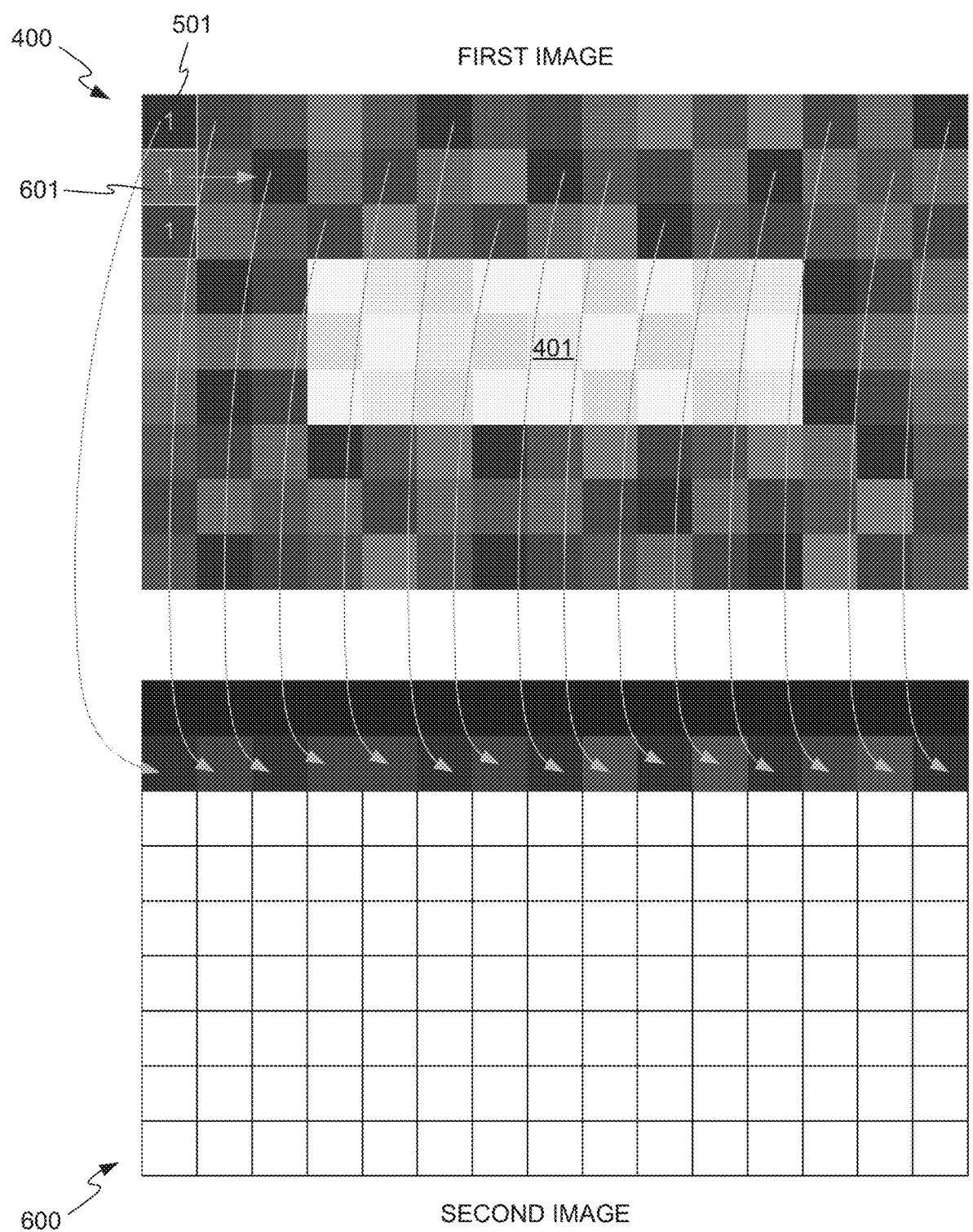
FIG. 6 illustrates the morphological operation of erosion.

FIG. 6 illustrates the morphological operation of erosion. Kernel 501 has been conceptually centered on pixel 601. The non-zero elements of kernel 500 define the "neighborhood" of pixels that will be affected at each application of kernel 500 in the erosion operation—that is, the top three pixels in the leftmost column of first image 400. The pixel in the defined neighborhood having the lowest intensity (the darkest of the three pixels in this example) is copied to the corresponding location in a second image 600. Kernel 500 is then conceptually moved across first image 400, and the neighborhood pixel having the lowest intensity at each kernel location is copied to the corresponding pixel of second image 600. This process proceeds row-by-row down image 400.

In the example of FIG. 6, first image 400 has been assumed to be surrounded by pixels have zero intensity, so centering kernel 500 on any pixel in the top row of image 400 will result in copying a pixel of zero intensity to the corresponding location in image 600. The top row of image 600 is shown has having been already processed in this way. In other embodiments, different assumptions may be used for handling the edge rows of image 400. For example, image 400 may be assumed to be padded with additional copies of its edge pixels, so that any theoretical pixel outside the boundary of image 400 will be similar to nearby pixels within the boundaries of image 400. Other ways of handling the edges of image 400 may be envisioned. FIG. 6 shows the result of traversing the first two rows of image 400 and copying the appropriate pixels.

Figure 7:
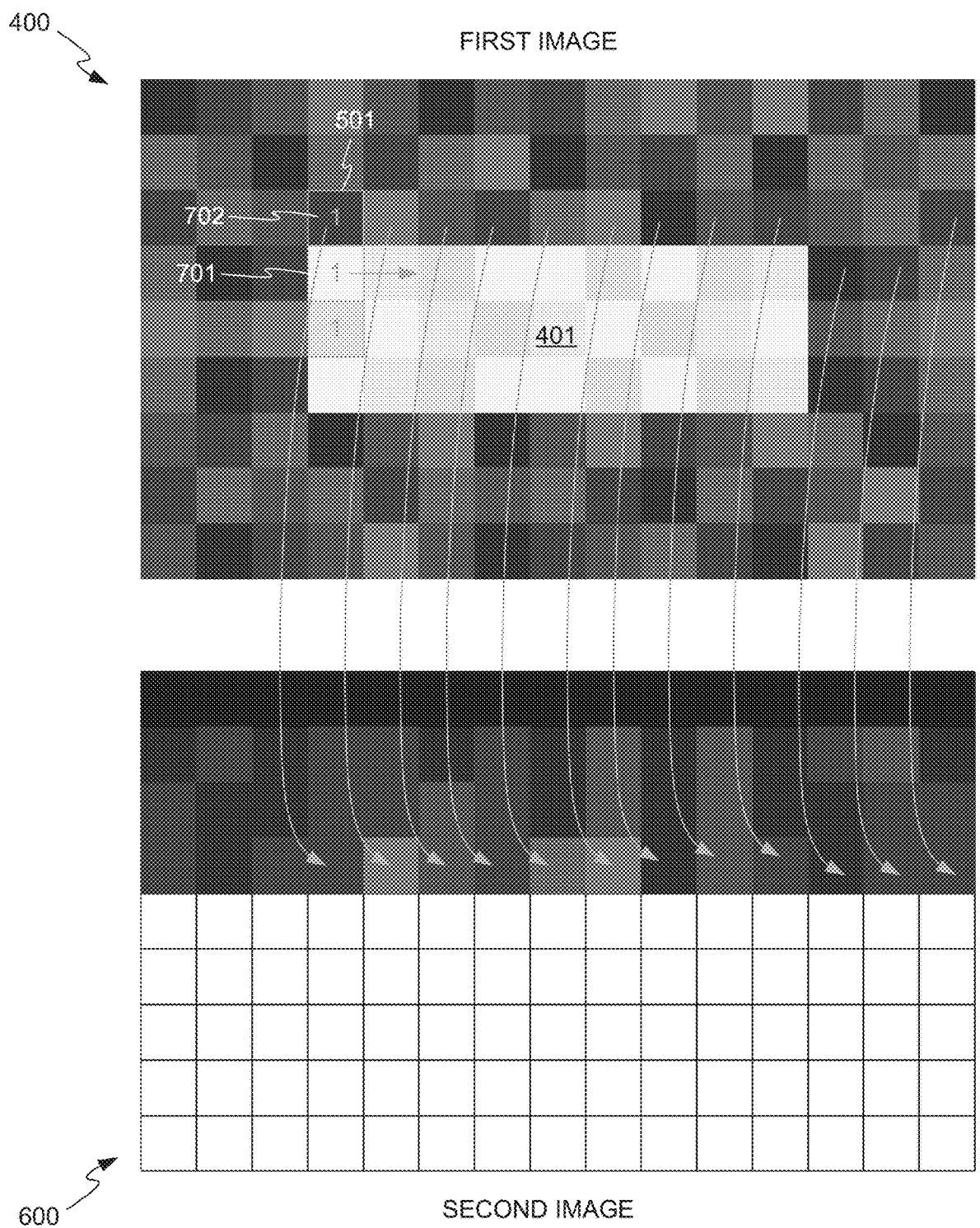
FIG. 7 illustrates a stage in the erosion process.

FIG. 7 illustrates what happens when the erosion process reaches feature 401. With kernel 501 centered on the upper left pixel 701 of higher-intensity feature 401, two of the three pixels in the neighborhood defined by kernel 501 are high-intensity pixels within feature 401. Thus, the lower-intensity (darker, in this example) pixel 702 is copied into second image 600. As kernel 501 proceeds across image 400 and along feature 401, the top pixels encompassed by kernel 501 are copied to image 600.

Figure 8:
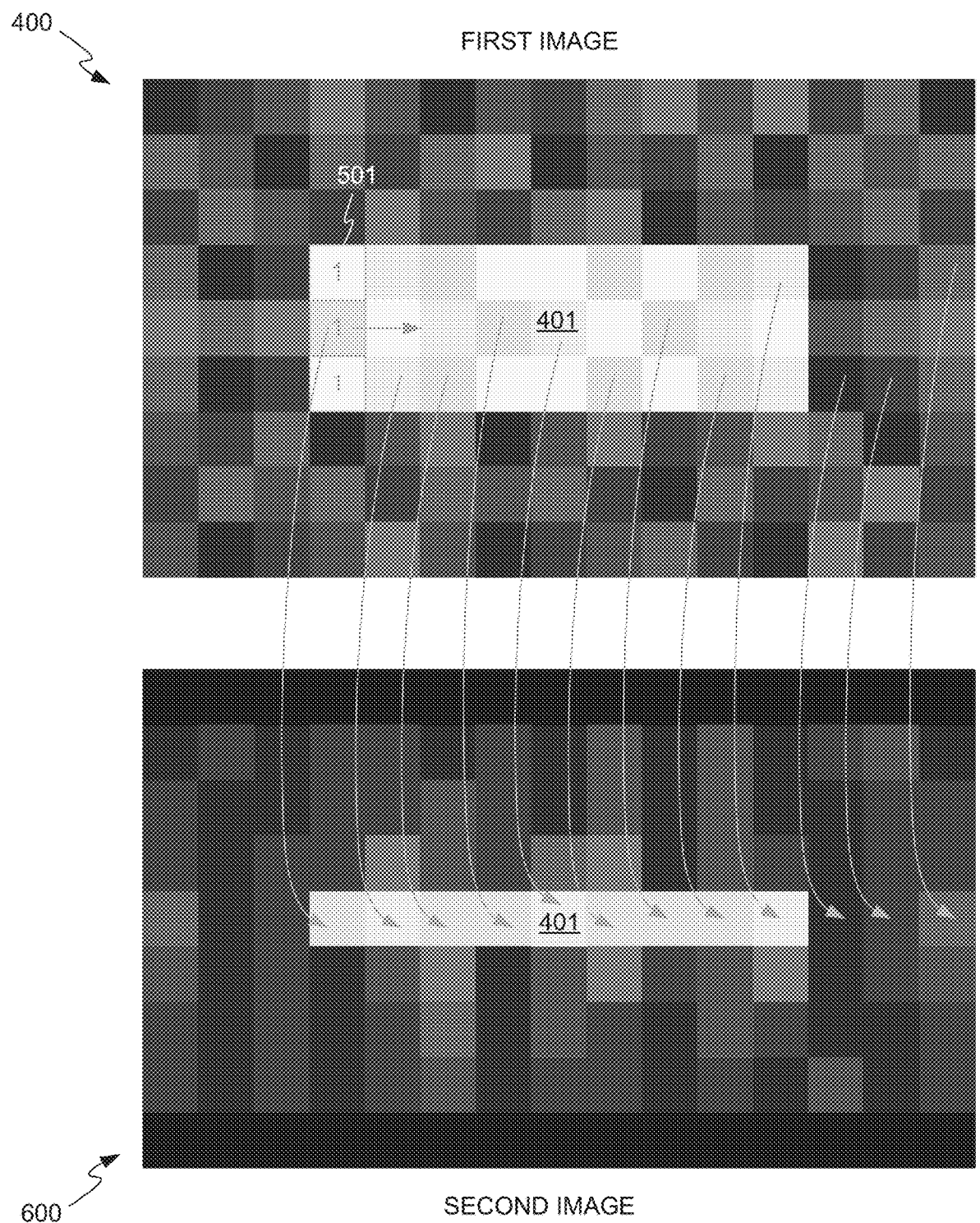
FIG. 8 illustrates another stage in the erosion process.

FIG. 8 illustrates processing the next row of image 400, in which kernel 501 is at times centered within feature 401. As kernel 501 traverses feature 401, only pixels from within feature 401 are copied, resulting in the copying of high-intensity pixels to image 600.

The remaining pixels are also shown in FIG. 8 as having been processed. As is apparent, the remaining vestige of high-intensity feature 401 in image 600 is narrower in height than in image 400, its top and bottom rows having been replaced by lower-intensity pixels. That is, the upper and lower edges of feature 401 appear to have been eroded away. (Because kernel 501 defines a single-column neighborhood, the width of feature 401 is substantially unaffected by the erosion process.) If the entire erosion process were to be applied to image 600 again, feature 401 would be entirely removed and replaced by lower-intensity pixels.

Figure 9:
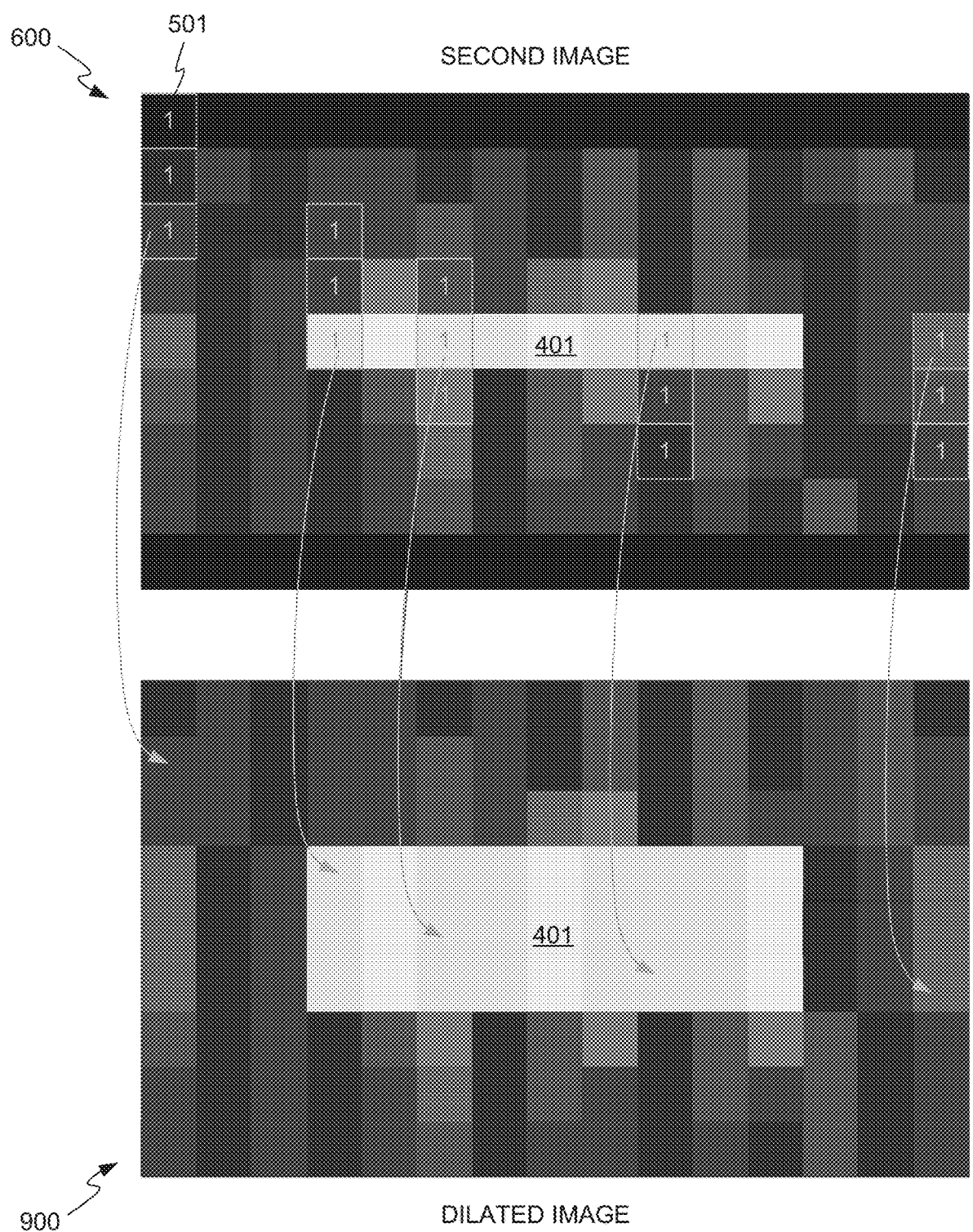
FIG. 9 illustrates the morphological process of dilation.

FIG. 9 illustrates the morphological process of dilation. Dilation is substantially the inverse of erosion. That is, in dilation, for each pixel location in the first image, the pixel having the highest intensity in the neighborhood defined by the kernel is copied to the target image. In erosion, high-intensity features tend to become smaller as they are eroded away. In dilation, high-intensity features tend to grow.

In FIG. 9, a few representative placements of kernel 501 are shown and their corresponding pixel copying results. The rest of dilated image 901 is completed in the same manner without showing the individual steps, for brevity. In completed dilated image 900, high-intensity feature 401 has been seen to grow, or dilate, as compared with its size in second image 600.

It is to be understood that the examples shown in FIGS. 4-9 are but one example of performing erosion and dilation. In other embodiments, kernels of different sizes or shapes may be used, different assumptions may be used for treatment of edge pixels, the process may be carried out in a more algorithmically efficient manner than simply marching through the image left-to-right and top-to-bottom, or other differences may be present. In some embodiments, higher intensity pixels may be represented as darker than lower intensity pixels.

As is discussed above, eroding an image a sufficient number of times can completely remove high-intensity features. Once the high-intensity features have been removed, then re-dilating the image an equal number of times will tend to spread the remaining low-intensity pixel values through the image. If it is assumed that the high-intensity features visible in a digital image represent actual features of interest in a blot and that the surrounding lower-intensity areas represent background signal, then this sequence of erosion and dilation provides a way of separating the actual blot features from the background signal.

For example, FIG. 10 shows original blot image 100 again, for convenient reference. FIG. 11 shows image 1100, which is the result of performing erosion on image 100 a sufficient number of times to completely remove features 101, and an equal number of dilations. As can be seen, while the erosion and dilation have a dramatic effect on features 101, the effect on the background areas of the image is relatively minor.

FIG. 12 shows an image 1200, which is the result of subtracting image 1100 from image 100. In this context, to "subtract" two digital images means to subtract the pixel values of one image from the pixel values of the other image, pixel-by-pixel. As can be seen in FIG. 12, the effect of the subtraction is to substantially remove the background signal from image 100, while leaving the features of interest in nearly their original state.

Figure 13:
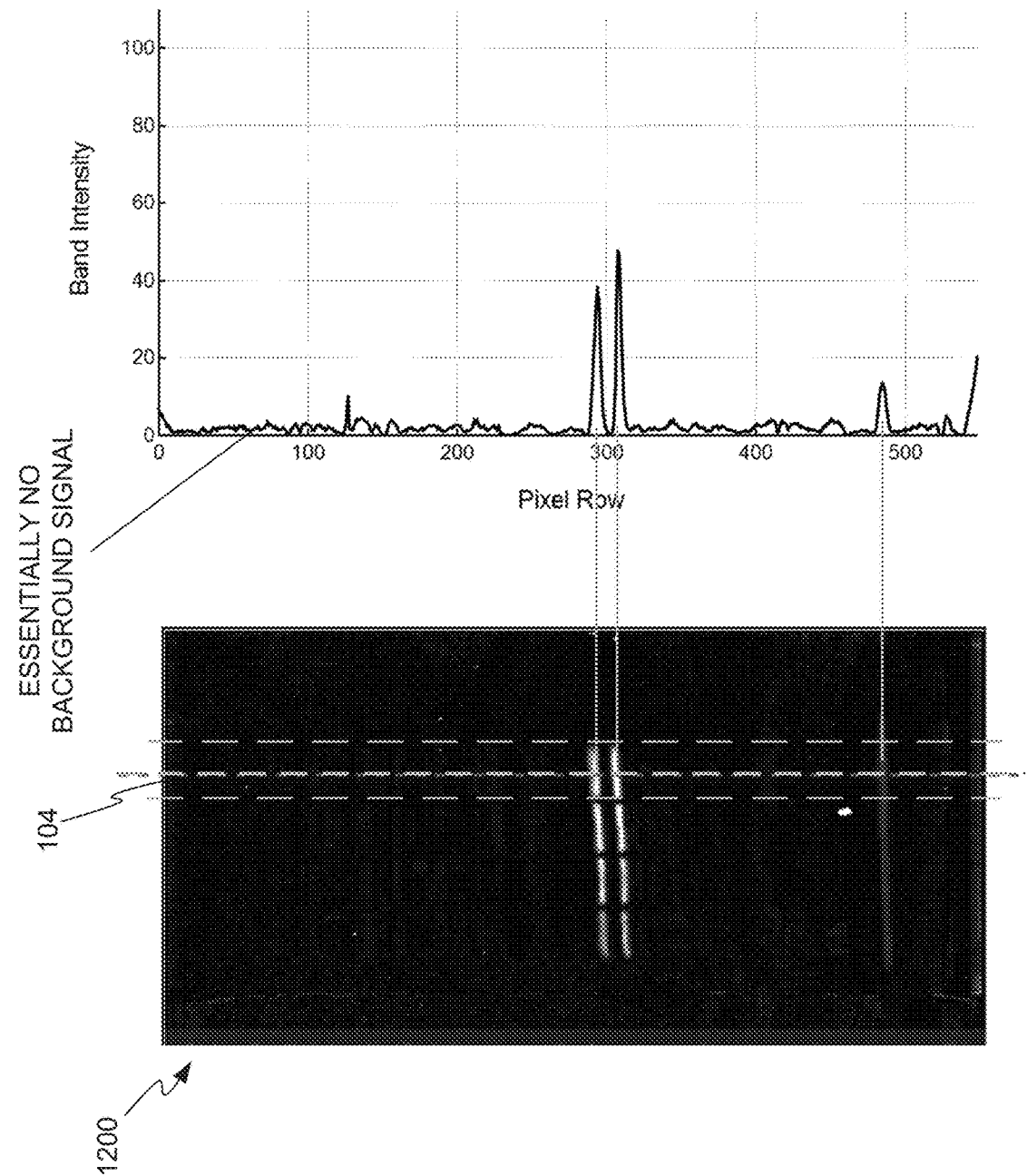
FIG. 13 shows the image of FIG. 12 with an intensity trace through one lane, in accordance with embodiments of the invention.

FIG. 13 shows image 1200 along with an intensity trace through column 104. As can be seen, there is essentially no background signal present, as compared with original image 100 as shown in FIG. 1.

As is described above, in order to produce image 1100, image 100 was eroded and dilated a "sufficient" number of times to remove features 101. Preferably, the number of erosions required to completely erode features 101 is determined automatically. In some embodiments, automatically determining when the features of interest have been completely eroded comprises performing increasing or otherwise varying numbers of erosions and dilations, and analyzing the resulting images.

Figure 14:
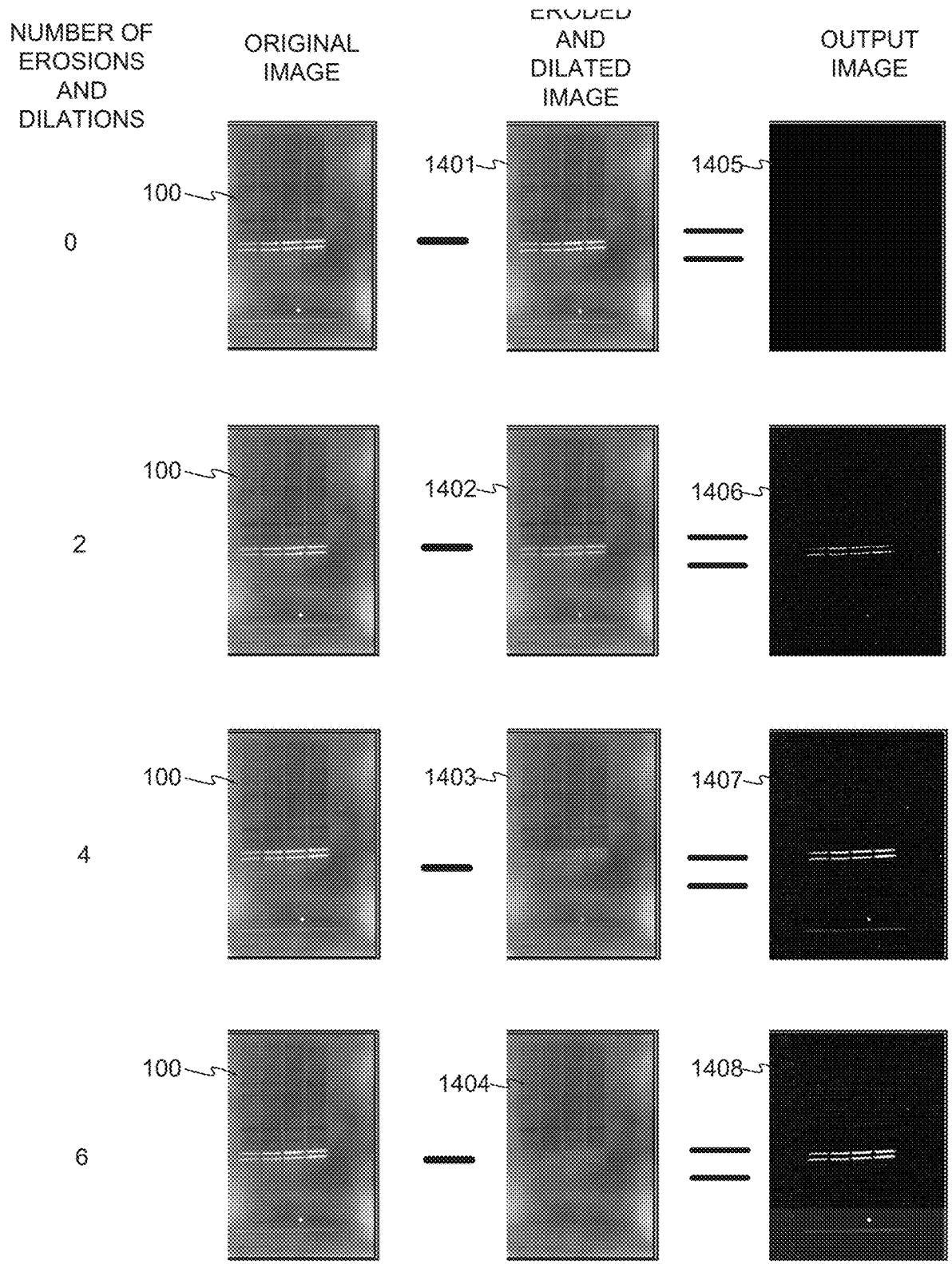
FIG. 14 illustrates the effect of increasing numbers of erosions and dilations on the image of FIG. 1, in accordance with embodiments of the invention.

FIG. 14 illustrates the effect of increasing numbers of erosions and dilations on image 100, in accordance with embodiments of the invention. In the top row of FIG. 14, no erosions and dilations are performed, so eroded and dilated image 1401 is identical to original image 100. Output image 1405 is completely dark, as the subtraction of image 1401 from image 100 results in the pixel-by-pixel subtraction of identical values, so that all of the differences are zero.

In the second row of FIG. 14, two erosions and dilations have been performed before the subtraction. The erosions and dilations have somewhat reduced the size and intensity of the higher-intensity features in image 1402, so that the subtraction of image 1402 from image 100 leaves some vestiges of the features in output image 1406. Similarly, four erosions and dilations are done to produce image 1403, and six erosions and dilations are done to produce image 1404. Accordingly, the high-intensity features become more prominent in output images 1407 and 1408 as the number of erosions and dilations increase.

However, if higher numbers of erosions and dilations were to be performed, more gradual continuing change would be observed in the output images, because the eroded and dilated images do not change as dramatically once complete erosion of the high-intensity features is reached.

One convenient way to characterize the change in the images as a function of the number of erosions and dilations is to compute the kurtosis of the output image at each stage of the process. The kurtosis of a digital image relates to the fourth moment of the brightness histogram. One common definition of kurtosis is $$\text{kurtosis} = \frac{\sum_{i=1}^{N}(Y_i - \mu)^4/N}{s^4}$$

where $\mu$ is the mean of the pixel brightness values in the image, $Y_i$ is the brightness of an individual pixel, N is the number of pixels in the image, and s is the standard deviation of the pixel brightness values in the image. Kurtosis is sometimes described as indicating the "tailedness" of a distribution, as compared with a normal distribution. In an image processing context, this means that a small number of pixels with either much higher or much lower intensities than the average intensity in the image will increase the kurtosis value of the image, as compared with an image in which the intensity histogram has smoothly decreasing tails.

Figure 15:
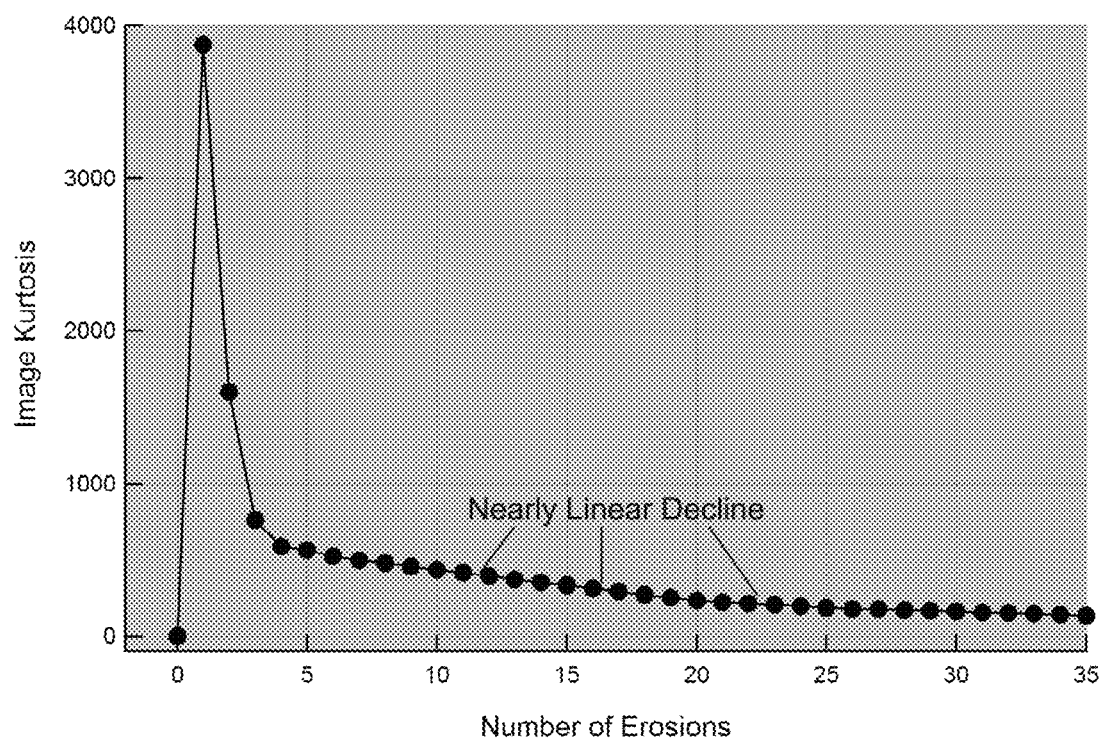
FIG. 15 illustrates the kurtosis values of images resulting from different numbers of erosions and dilations, in accordance with embodiments of the invention.

FIG. 15 illustrates the kurtosis values of images resulting from different numbers of erosions and dilations, in accordance with embodiments of the invention. Some of the points in FIG. 15 correspond to images 1405-1408 shown in FIG. 14. While uniform image 1405 has zero kurtosis, the other images have non-zero kurtosis. The kurtosis declines rapidly after one erosion and dilation, but the rate of decline decreases in magnitude as more erosions and dilations are performed. The continuing decline after large numbers of erosions and dilations can be understood by recognizing that the erosion and dilation cycles tend to narrow the histogram of the eroded and dilated image. Erosions tend to replace the highest-intensity pixels with pixels of lower intensity, and dilations tend to replace the lowest-intensity pixels with pixels of higher intensity. The narrower the histogram of the eroded and dilated image, the less the subtraction operation widens the histogram of the output image.

Figure 16:
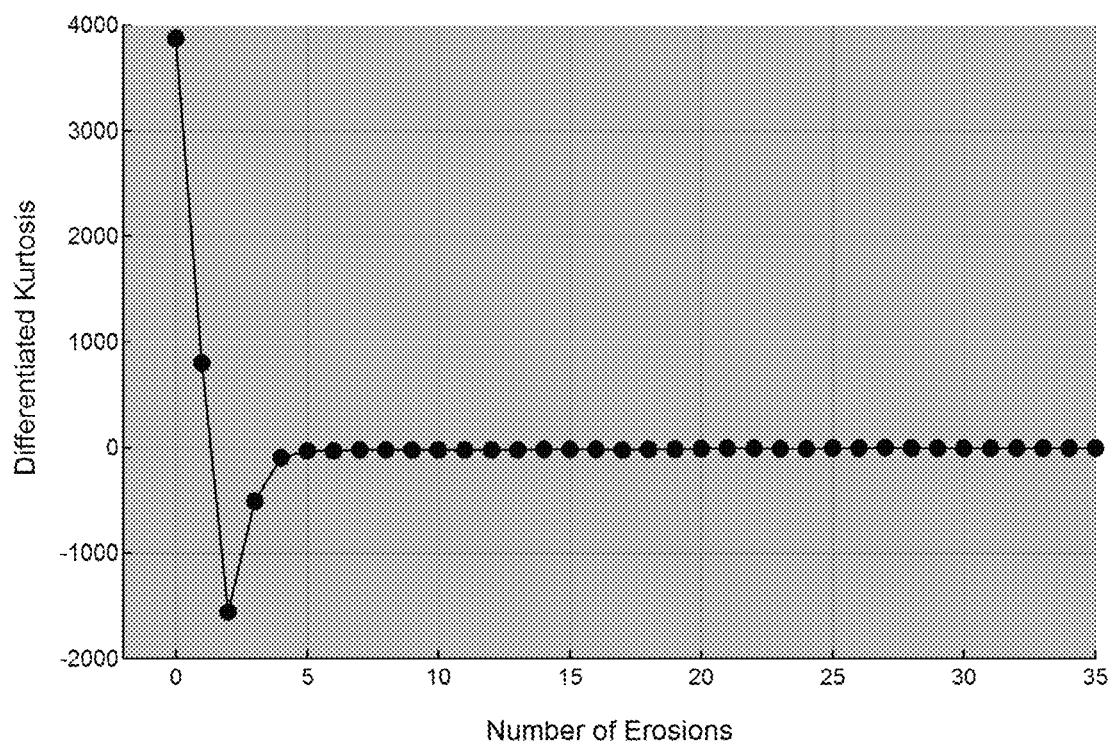
FIG. 16 shows an approximated derivative of the kurtosis curve of FIG. 15, in accordance with embodiments of the invention.

This effect is illustrated in FIG. 16, showing an approximate derivative of the kurtosis curve of FIG. 15 in accordance with embodiments of the invention. The derivative is approximated by differences between adjacent values of the kurtosis. After an initial positive jump, the differentiated kurtosis approaches a small negative value, reflecting the nearly linear decline of the kurtosis value as shown in FIG. 15.

Figure 17:
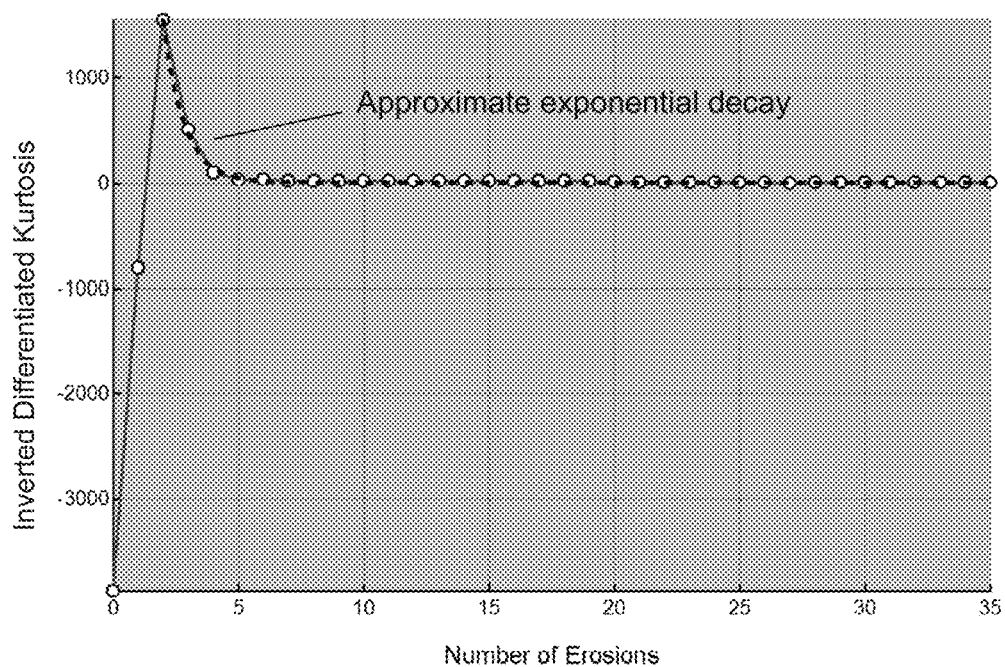
FIG. 17 shows an inversion of the curve of FIG. 16, in accordance with embodiments of the invention.

It may be convenient to invert the differentiated kurtosis curve (subtract each of the values from zero), and the inverted curve is shown in FIG. 17, in accordance with embodiments of the invention. As can be seen in FIG. 17, the decline in the differentiated kurtosis is approximately exponential after the initial jump. In embodiments of the invention, the rate of change in kurtosis can be exploited to automatically determine how many erosions are "sufficient" to completely erode the high-intensity features of interest from a blot image.

Figure 18:
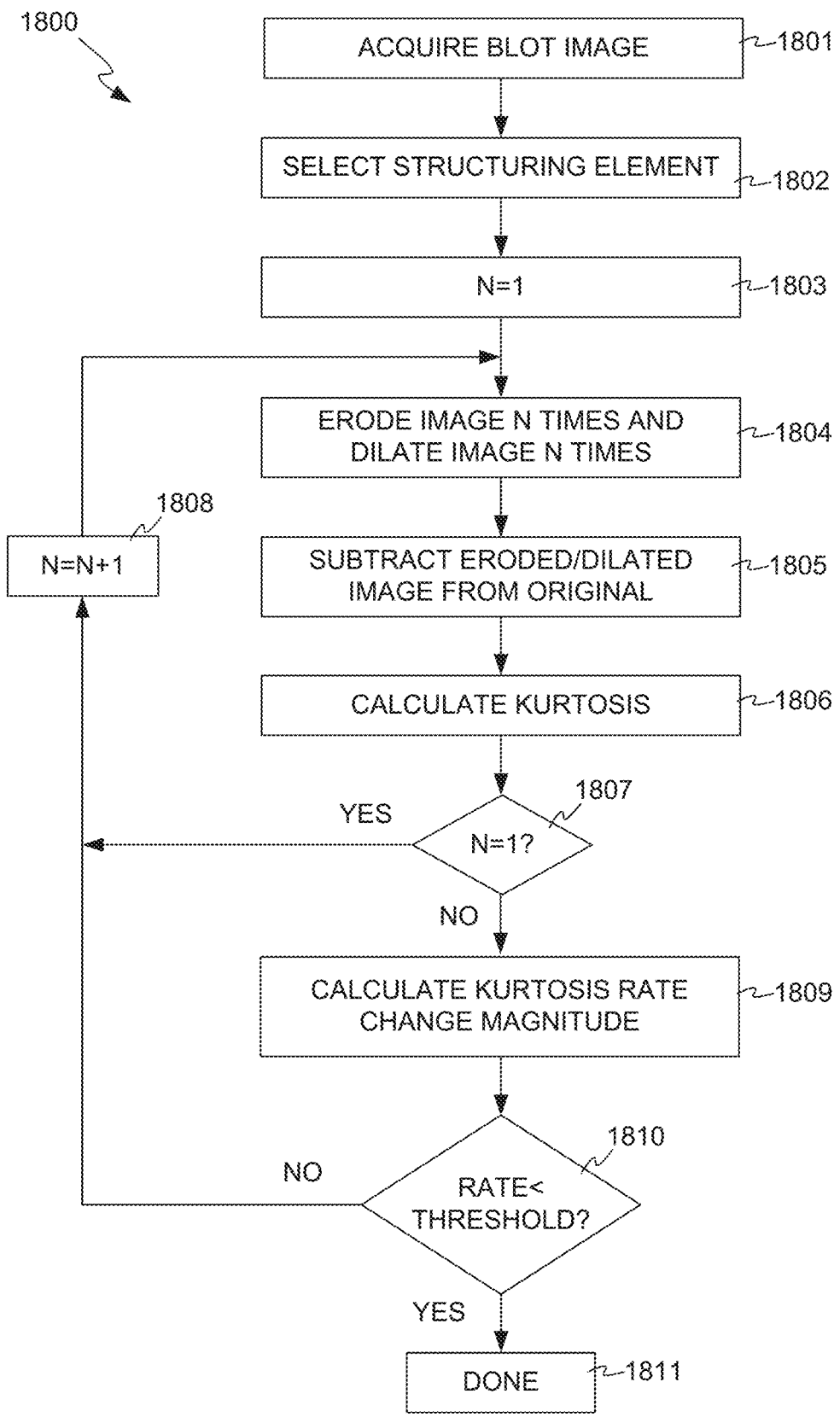
FIG. 18 illustrates a flowchart of a method in accordance with embodiments of the invention.

For example, in one embodiment, erosion-dilation-subtraction cycles may be conducted using increasing numbers of erosions until the rate of change of kurtosis is smaller in magnitude than a predetermined threshold. FIG. 18 illustrates a flowchart 1800 of this technique. In step 1801, a digital blot image is acquired using an imaging system such as imaging system 200 or imaging system 300 described above, or another suitable imaging system. The imaging system has a field of view and a magnification. The digital image includes features of interest, and the sizes of the features of interest in the digital image are determined in part by the magnification of the imaging device, and the shapes of the features of interest in the digital image are determined in part by a particular technique used to produce the blot. In step 1802, a structuring element is selected having a size and shape selected at least in part based on the sizes and shapes of the features of interest in the digital image. For example, the features of interest in an image of a western blot may be generally rectangular, and an appropriate structuring element may be a vertical column such as structuring element 501 described above.

In step 1803, a counter N is initialized. In steps 1804 and 1805, the blot image is eroded and dilated N times, and then subtracted from the original blot image to produce an output image. At step 1806, the kurtosis of the output image is calculated. At step 1807, if N=1, the counter N is incremented at step 1808 and control passes back to step 1804. Otherwise, the rate of change of the kurtosis of the output image is calculated at step 1809. At step 1810, the rate of change of the kurtosis is compared with a predetermined threshold. If the kurtosis is still changing rapidly as a function of the number of erosions, counter N is incremented at step 1808 and control passes back to step 1804.

However, if the magnitude of the rate of change of the kurtosis has fallen below the threshold, it is assumed that the features of interest were completely removed from the eroded and dilated image produced in step 1804, and that the output image has therefore had any background signal substantially removed. The method of FIG. 18 stops at step 1811, with the output image being the desired output image.

Figure 19:
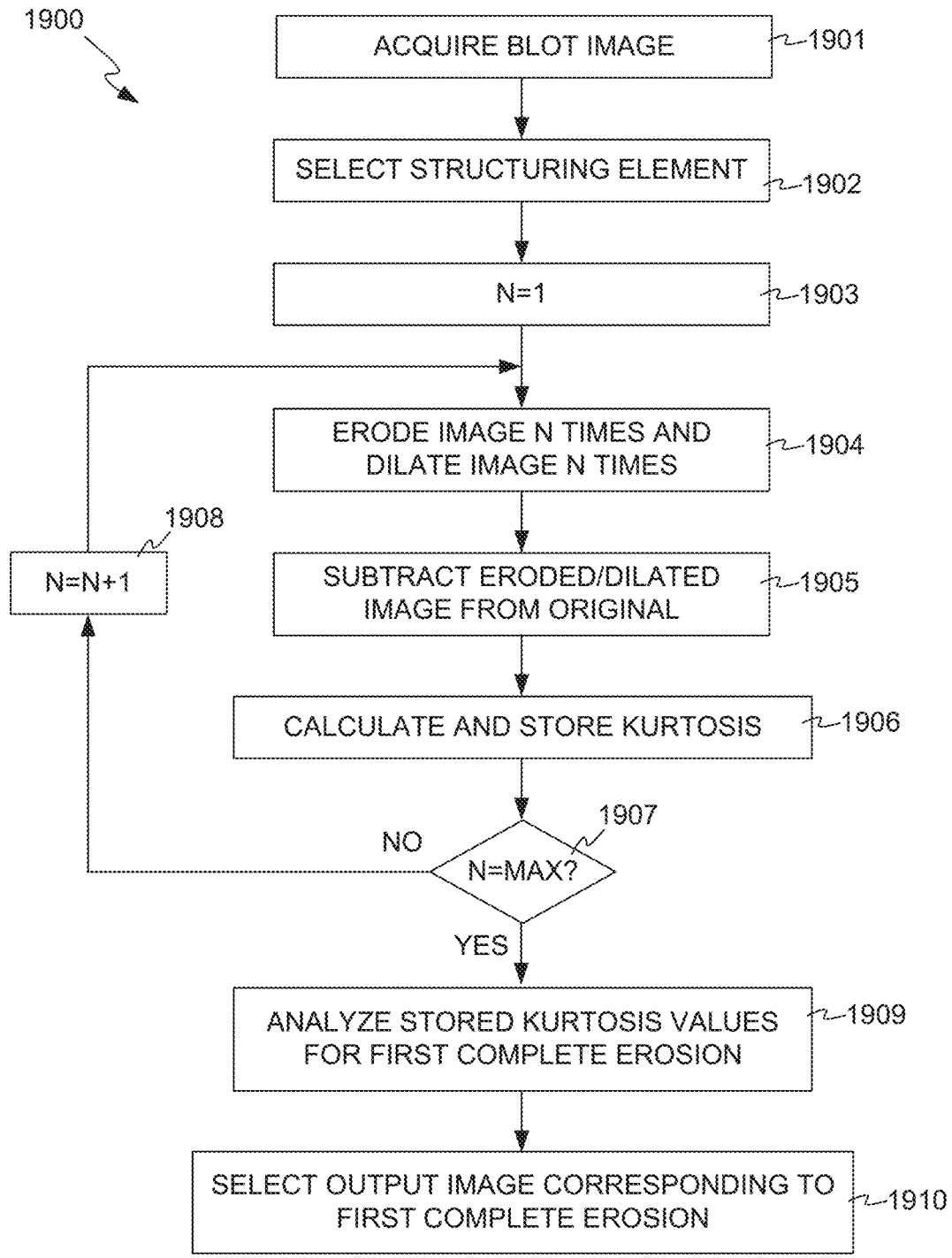
FIG. 19 illustrates a flowchart of another method in accordance with embodiments of the invention.

In another and possibly more robust technique, the rate of change of the image kurtosis may be analyzed in more detail to determine when a sufficient number of erosions have been performed to substantially remove the features of interest from the eroded and dilated image. FIG. 19 shows a flowchart of a method in accordance with other embodiments.

Steps 1901, 1902, and 1903 may be similar to steps 1801, 1802, and 1803 described above. That is, a blot digital image is similarly acquired and a structuring element is similarly selected, and a counter N is initialized. Likewise, steps 1904 and 1905 may be similar to steps 1804 and 1805, in that the blot image is eroded and dilated N times, and the resulting eroded and dilated image is subtracted from the original blot image to generate an output image.

At step 1906, the kurtosis of the output image is calculated and stored. If N has not reached a preselected maximum (step 1902), then N is incremented at step 1908 and control passes again to step 1904. Steps 1903-1908 thus form a "do loop" in which the original image is eroded and dilated increasing numbers of times, each eroded and dilated image is subtracted from the original image to produce and output image, and the kurtosis values of the output images are stored, for example in an array of values.

While the example of FIG. 19 shows N incrementing by one at each iteration, in other embodiments, N may be incremented more quickly after a few iterations of the loop. For example, N may be incremented by one until N=10 is reached, and N may be incremented by fives in subsequent iterations. This technique may save unnecessary calculation and make the method more robust to noise, as the kurtosis values may change slowly after the first few iterations. Preferably, the value of N is allowed to exceed the number of erosions needed to completely erode the features of interest in the blot image. For example, the maximum value of N tested in step 1907 may be up to 50 or more. That is, in the final iteration of FIG. 19, the blot image may be eroded 50 times or more and dilated an equal number of times in producing the last output image. Any suitable maximum number of erosions and dilations may be used, and may be more or less than 50. In other embodiments, the sets of erosions and dilations need not be performed in increasing sequence, but may use any variation pattern.

Once all of the kurtosis values are stored, they are analyzed at step 1909 to determine at what point (what value of N) the image was first completely eroded. At step 1910, the output image corresponding to this value of N is determined to be the desired output image. In other embodiments, a somewhat later output image may be selected, for example the next image after the image determined to be the first completely eroded image.

The analysis performed at step 1909 may take any suitable form. For example, an exponential decay curve may be mathematically fit to the declining inverted differentiated kurtosis values such as are shown in FIG. 17. The curve fit is defined from the max value (of differentiated kurtosis), to the final kurtosis value. A convenient curve will be of the form $$y = y_0 + A * \exp(-k*x).$$

The term k represents the rapidity of the decay, and is sometimes called the exponential decay constant. In some embodiments, the curve may be considered to have nearly fully decayed—indicating that the kurtosis is changing sufficiently slowly and the image has been completely eroded—after a specified number of exponential decay constants, for example three, four, or another suitable exponential decay constants after the initial value used in the image. For example if k=2.8 and a criterion of four exponential decay constants is used, then the 11$^{th}$ output image will be selected as the desired output image (2.8*4~11).

The term $y_0$ in the above formula accounts for the fact that the kurtosis of the image may decline slowly for large numbers of erosions, and the rate of decay may not reach zero within the maximum number of erosions performed. In another embodiment, the logarithm of each of the differentiated kurtosis values approximated by the fitted curve may be taken, and a straight line fit to the resulting curve. Because the fitted decay curve is an exponential (with a small ordinate offset), the logarithm values will form approximately a straight line.

Figure 20:
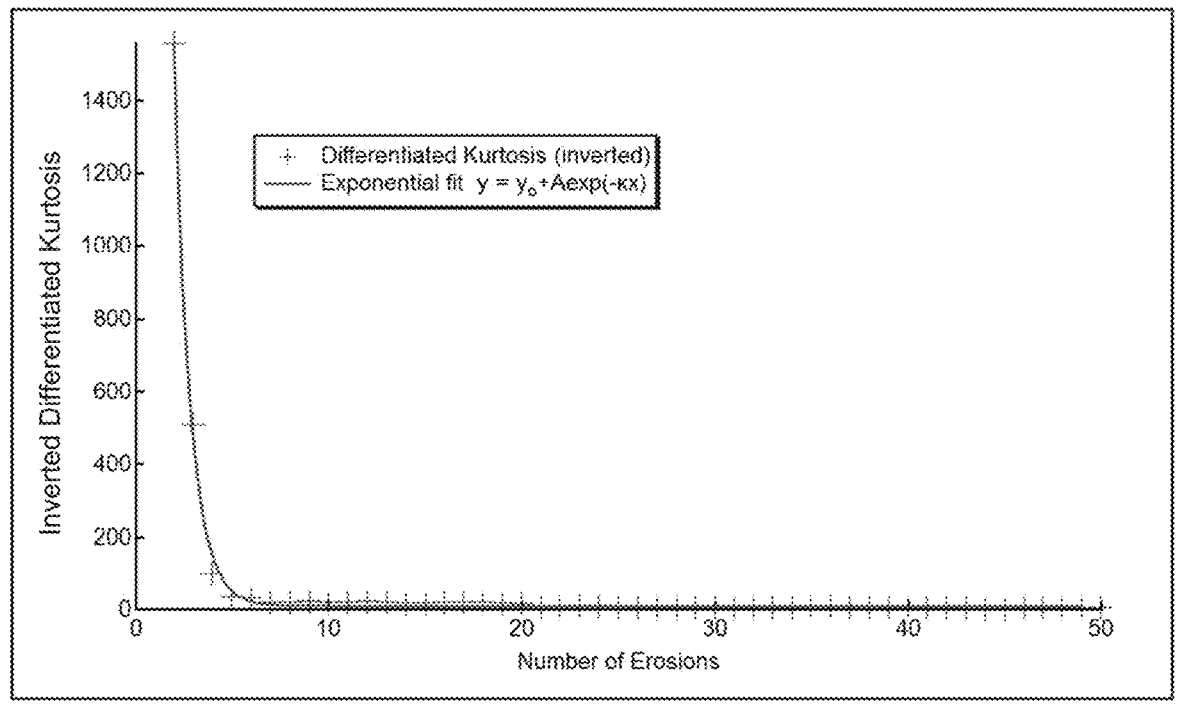
FIG. 20 illustrates the fit of a curve to the differentiated kurtosis values generated from the image of FIG. 1.
Figure 21:
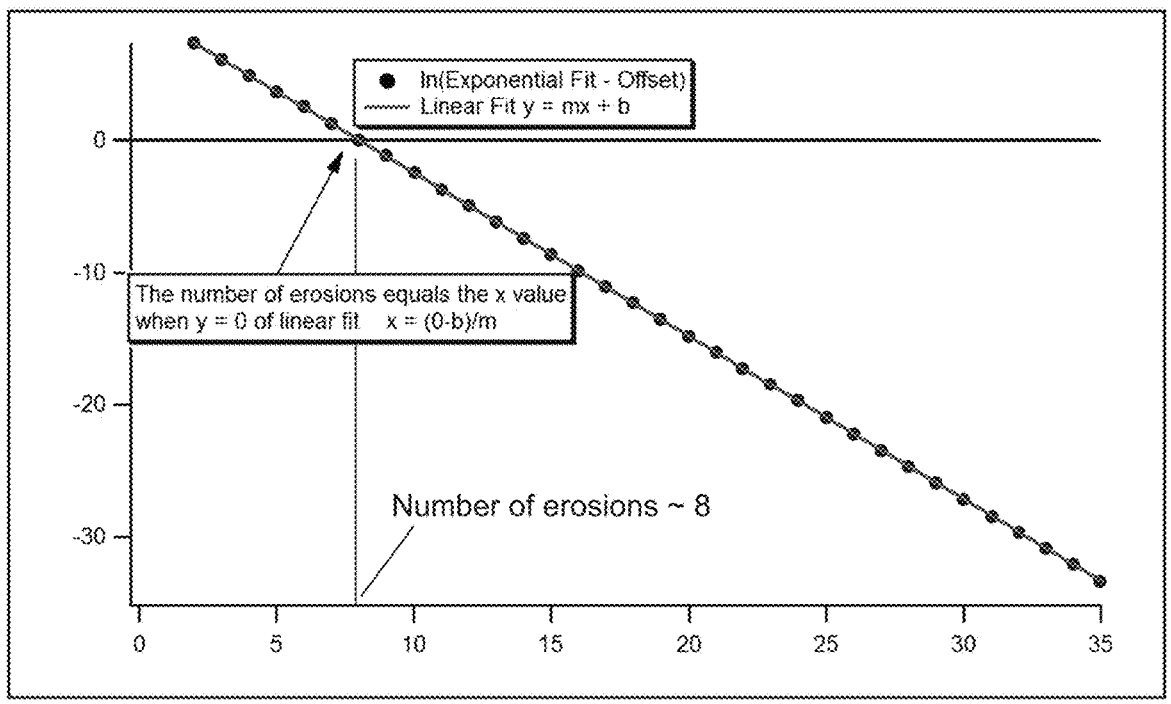
FIG. 21 shows the logarithms of points on the fitted curve of FIG. 20, as well as a line fitted to the logarithms

FIG. 20 illustrates the fit of a curve of the form $y=y_0+A*exp(-k*x)$ to the differentiated kurtosis values generated from image 100. FIG. 21 shows the logarithms of points on the fitted curve, as well as a line fitted to the logarithms. In the example of FIG. 21, the best fit line intersects the horizontal axis after about eight erosions, so the output image generated using eight erosions and dilations is selected as the desired image. In other embodiments, an output image near the eighth image may be selected, for example the ninth or seventh output image.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A method of removing background from a digital image of a biological blot, the method comprising:
   receiving a first digital image of a biological blot having features of interest, the first digital image produced by an imaging device having a field of view and a magnification, the digital image including the features of interest, wherein the sizes of the features of interest in the first digital image are determined in part by the magnification of the imaging device, and the shapes of the features of interest in the first digital image are determined in part by a particular technique used to produce the blot;
   selecting a structuring element, the size and shape of the structuring element being selected at least in part based on the sizes and shapes of the features of interest in the first digital image;
   performing sets of morphological erosions and dilations of the first digital image, wherein performing a set of morphological erosions and dilations comprises:
      performing morphological erosion of the first digital image using the structuring element to produce a second digital image, the morphological erosion being performed a number of times; and
      subsequently performing morphological dilation of the second digital image using the structuring element to produce an eroded and dilated image, the morphological dilation being performed the same number of times as the morphological erosion;
   producing an output digital image by subtracting the eroded and dilated digital image from the first digital image;
   wherein the erosions and dilations are performed in sets having increasing numbers of erosions and dilations;
   and wherein the method further comprises automatically determining after each set of erosions and dilations whether the features of interest have been completely eroded, to determine the number of erosions needed to completely erode the features of interest, and wherein automatically determining whether the features of interest have been completely eroded comprises automatically determining whether the features of interest have been completely eroded based on a kurtosis of the output image.

2. The method of claim 1, wherein the imaging device is a camera.

3. The method of claim 1, wherein the imaging device is a scanner or densitometer.

4. The method of claim 1, wherein the blot emanates light by fluorescence, and wherein the imaging device produces the first digital image by measuring the light emanated from the blot by fluorescence.

5. The method of claim 1, wherein the blot emanates light by chemiluminescence, and wherein the imaging device produces the first digital image by measuring the light emanated from the blot by chemiluminescence.

6. The method of claim 1, wherein automatically determining whether the features of interest have been completely eroded further comprises:
   producing a respective output image after each set of erosions and dilations;
   calculating a kurtosis of the respective output image after each set of erosions and dilations;
   tracking the rate of change of the kurtosis as a function of the number of erosions and dilations in each set of erosions and dilations;
   comparing the rate of change of the kurtosis with a predetermined threshold; and
   determining that the features of interest have been completely eroded when the rate of change of the kurtosis falls below the predetermined threshold.

7. The method of claim 1, further comprising:
   producing a respective output image after each set of erosions and dilations;
   calculating a kurtosis of the respective output image after each set of erosions and dilations; and
   modeling the rate of change of the kurtosis as an exponential decay of the rate as a function of the number of erosions and dilations in each set of erosions and dilations.

8. The method of claim 7, further comprising:
   fitting a straight line to the logarithms of at least some of the measured rates of change of kurtosis as a function of the number of erosions and dilations performed in each set of erosions and dilations; and
   calculating where the straight line has a zero ordinate.

9. The method of claim 8, further comprising selecting as a desired output image the output image corresponding to the number of erosions and dilations at which the straight line has a zero ordinate.

10. The method of claim 1, wherein receiving a first digital image of a biological blot comprises receiving a digital image of an electrophoretic sample.

11. The method of claim 10, wherein the sizes and shapes of the features of interest in the first digital image are determined at least in part by the particular electrophoretic technique used to prepare the blot.

12. The method of claim 1, wherein receiving a first digital image of a biological blot comprises receiving a digital image of a western blot.

13. The method of claim 1, wherein receiving a first digital image of a biological blot comprises receiving a digital image of a dot blot.

14. A method of removing background from a digital image of a biological blot, the method comprising:
   receiving a first digital image of a biological blot having features of interest;
   selecting a structuring element, the size and shape of the structuring element being selected at least in part based on the sizes and shapes of the features of interest in the first digital image;
   performing morphological erosion of the first digital image using the structuring element to produce a second digital image, the morphological erosion being performed;
   subsequently performing morphological dilation of the second digital image using the structuring element to produce an eroded and dilated image, the morphological dilation being performed the same number of times as the morphological erosion;
   producing an output digital image by subtracting the eroded and dilated digital image from the first digital image; and
   automatically determining that the features of interest have been completely eroded from the first digital image based on a kurtosis of the output image.

15. The method of claim 14, wherein an equal number of erosions and dilations constitute a set of erosions and dilations, and the erosions and dilations are performed in sets having increasing numbers of erosions and dilations, and wherein the method further comprises:
   producing a respective output image after each set of erosions and dilations;
   calculating a kurtosis of the respective output image after each set of erosions and dilations; and
   determining whether the features of interest have been completely eroded from a particular one of the respective output images based on the behavior of the kurtosis as a function of the number of erosions and dilations in each set of erosions and dilations.

16. The method of claim 15, wherein determining whether the features of interest have been completely eroded from a particular one of the respective output images based on the behavior of the kurtosis as a function of the number of erosions and dilations in each set of erosions and dilations comprises:
   calculating a rate of change of the kurtosis as a function of the number of erosions and dilations in each set of erosions and dilations; and
   determining whether the features of interest have been completely eroded from a particular one of the output images based on the behavior of the rate of change of the kurtosis as a function of the number of erosions and dilations in each set of erosions and dilations.

17. The method of claim 1, further comprising producing a respective output image after each set of erosions and dilations, wherein automatically determining after each set of erosions and dilations whether the features of interest have been completely eroded comprises automatically determining whether the features of interest have been completely eroded based on a kurtosis of the respective output image.

* * * * *